(12) United States Patent
Lyu et al.

(10) Patent No.: US 12,616,185 B2
(45) Date of Patent: May 5, 2026

(54) AROMATHERAPY MOSQUITO KILLER

(71) Applicant: Zhejiang Xiaozheng Technology Co., Ltd, Ningbo (CN)

(72) Inventors: Lingling Lyu, Ningbo (CN); Jun Zheng, Ningbo (CN); Yuanai Ning, Ningbo (CN)

(73) Assignee: Zhejiang Xiaozheng Technology Co., Ltd., Ningbo (CN)

( * ) Notice: Subject to any disclaimer, the term of this patent is extended or adjusted under 35 U.S.C. 154(b) by 0 days.

(21) Appl. No.: 18/800,163

(22) Filed: Aug. 12, 2024

(65) Prior Publication Data

US 2025/0057143 A1    Feb. 20, 2025

(51) Int. Cl.
*A01M 1/08*        (2006.01)
*A61L 9/12*        (2006.01)

(52) U.S. Cl.
CPC .............. *A01M 1/08* (2013.01); *A61L 9/122* (2013.01); *A01M 2200/012* (2013.01)

(58) Field of Classification Search
CPC ..................................................... A01M 1/08
See application file for complete search history.

(56) References Cited

U.S. PATENT DOCUMENTS 5,014,460 A  *  5/1991  Patti ........................ A01M 1/08
                                                        43/107
5,020,270 A  *  6/1991  Lo ........................... A01M 1/08
                                                        43/112

5,255,468 A  *  10/1993  Cheshire, Jr. ........... A01M 1/06
                                                        43/112
5,417,009 A  *  5/1995  Butler .................... A01N 43/16
                                                        43/113
6,134,826 A  *  10/2000  Mah ....................... A01M 1/223
                                                        43/99
6,406,673 B1*  6/2002  Soller ................. A01M 1/2088
                                                        422/126
6,482,365 B1*  11/2002  Soller ................. A01M 1/2066
                                                        422/126
10,021,869 B1*  7/2018  Cogley ................... A01M 5/02
10,948,146 B2*  3/2021  Li ......................... F21V 23/001
                            (Continued)

FOREIGN PATENT DOCUMENTS

CN        109964916 A  *  7/2019  ............ A01M 29/12
CN        112400832 A  *  2/2021  ............ A01M 1/223
                            (Continued)

*Primary Examiner* — Morgan T Jordan

(57)        ABSTRACT

An aromatherapy mosquito killer includes a shell with a light chamber, a fan chamber and a mosquito killing chamber provided therein, a light module arranged in the light chamber for emitting light outwardly, a fan arranged in the fan chamber, and an aromatherapy box arranged in the mosquito killing chamber for collecting mosquitoes and storing aromatherapy. Airflow holes are defined in top and bottom sides of a chamber wall of the fan chamber. Ventilation holes are defined in a side wall and a top wall of the aromatherapy box. Air inlets and air outlets are defined in the shell. The air inlets, the airflow holes and the ventilation holes in the top wall of the aromatherapy box cooperatively form a mosquito-killing air duct for sucking in mosquitoes; and the ventilation holes in the side wall of the aromatherapy box cooperatively form an exhaust air duct.

13 Claims, 3 Drawing Sheets

(56) References Cited

U.S. PATENT DOCUMENTS

| | | | | |
|---|---|---|---|---|
| 2002/0066798 A1* | 6/2002 | Laudamiel-Pellet | ... | A61L 9/042 239/34 |
| 2003/0070346 A1* | 4/2003 | Winner | ................... | F23D 14/28 43/112 |
| 2003/0131525 A1* | 7/2003 | Bertani | ................... | A01M 1/08 43/139 |
| 2004/0068917 A1* | 4/2004 | Chan | ....................... | A01M 1/08 43/113 |
| 2004/0128904 A1* | 7/2004 | Chen | ....................... | A01M 1/08 43/139 |
| 2004/0148848 A1* | 8/2004 | Bertani | ................... | A01M 1/06 43/139 |
| 2004/0159040 A1* | 8/2004 | Chen | .................... | A01M 1/223 43/112 |
| 2004/0257798 A1* | 12/2004 | Hart | .................... | A01M 1/2044 362/96 |
| 2005/0074358 A1* | 4/2005 | Hart | .................... | A01M 1/2083 422/5 |
| 2005/0169812 A1* | 8/2005 | Helf | ..................... | G02B 6/0068 422/123 |
| 2006/0120080 A1* | 6/2006 | Sipinski | .................. | F21S 10/04 362/253 |
| 2006/0123694 A1* | 6/2006 | Welch | ................... | A01M 1/023 43/107 |
| 2007/0109782 A1* | 5/2007 | Wolf | ....................... | A61L 9/037 362/253 |
| 2008/0011875 A1* | 1/2008 | Sipinski | ............. | B05B 17/0684 239/326 |
| 2008/0066372 A1* | 3/2008 | Fleming | ............. | A01M 1/2083 43/113 |
| 2008/0073443 A1* | 3/2008 | Tollens | .............. | B05B 17/0646 222/638 |
| 2008/0168702 A1* | 7/2008 | Jaffrey | ................. | A01M 1/223 43/118 |
| 2008/0197213 A1* | 8/2008 | Flashinski | .......... | B05B 17/0684 239/288.5 |
| 2008/0315005 A1* | 12/2008 | Michaels | .................. | A61L 9/14 239/4 |
| 2009/0000183 A1* | 1/2009 | Geier | .................... | A01M 1/223 43/107 |
| 2009/0293341 A1* | 12/2009 | Fleming | .............. | A01M 1/2055 43/131 |
| 2011/0283597 A1* | 11/2011 | Coventry | ................ | A01M 1/08 43/107 |
| 2014/0137462 A1* | 5/2014 | Rocha | ................... | A01M 1/023 43/113 |
| 2016/0212984 A1* | 7/2016 | Fang | ..................... | A01M 1/023 |
| 2017/0258068 A1* | 9/2017 | Eom | ..................... | A01M 1/106 |
| 2018/0213763 A1* | 8/2018 | Lee | ........................ | F21V 23/00 |
| 2018/0279598 A1* | 10/2018 | Hur | ....................... | A01M 1/106 |
| 2019/0008132 A1* | 1/2019 | Eom | ....................... | A01M 1/06 |
| 2019/0090470 A1* | 3/2019 | Lee | .......................... | A01M 1/04 |
| 2019/0133106 A1* | 5/2019 | Eom | ....................... | A01M 1/08 |
| 2019/0159440 A1* | 5/2019 | Zheng | ................... | A01M 1/223 |
| 2020/0254851 A1* | 8/2020 | Nixon | ................... | B05B 11/06 |
| 2020/0375169 A1* | 12/2020 | Zheng | ................... | A01M 1/02 |
| 2021/0153493 A1* | 5/2021 | Zhang | ................... | A01M 1/08 |
| 2021/0400944 A1* | 12/2021 | Lee | ........................ | A01M 1/08 |
| 2022/0022441 A1* | 1/2022 | Dolshun | ................ | A01M 1/08 |
| 2022/0105224 A1* | 4/2022 | Vazquez Alvarez | .... | A61L 9/013 |
| 2022/0248654 A1* | 8/2022 | Howland | ............... | A01M 1/08 |
| 2022/0330536 A1* | 10/2022 | Zheng | ................... | A01M 1/14 |
| 2022/0362430 A1* | 11/2022 | Hasik | ................... | A01M 1/2044 |
| 2024/0042085 A1* | 2/2024 | Hasik | ..................... | A61L 9/037 |
| 2024/0215562 A1* | 7/2024 | Romanova | ........... | A01M 1/023 |

FOREIGN PATENT DOCUMENTS

| | | | | | | |
|---|---|---|---|---|---|---|
| CN | | 112772600 A | * | 5/2021 | ............. | A01M 1/08 |
| KR | | 20170112972 A | * | 10/2017 | ............. | A01M 1/10 |
| KR | | 20230020093 A | * | 2/2023 | ............. | A01M 1/06 |
| WO | WO-2018008923 A1 | | * | 1/2018 | ............. | A01M 1/08 |
| WO | WO-2018097631 A1 | | * | 5/2018 | ............. | A61L 9/20 |
| WO | WO-2019035683 A1 | | * | 2/2019 | ............. | A61L 9/205 |
| WO | WO-2021201639 A1 | | * | 10/2021 | ............. | A01M 1/106 |

* cited by examiner

AROMATHERAPY MOSQUITO KILLER

CROSS-REFERENCE TO RELATED APPLICATIONS

This application claims the priority of Chinese patent application No. 202322203641.4, filed on Aug. 16, 2023, the entire contents of which are hereby incorporated by reference.

TECHNICAL FIELD

The present application relates to the technical field of mosquito killers, in particular to an aromatherapy mosquito killer.

BACKGROUNDS

Mosquito killing lamps are mosquito killing devices that do not require the use of any chemical mosquito-killing substances. Generally, the mosquito killing lamp utilizes mosquito's habits of phototaxis, movement with airflow, sensitivity to temperature, preference for gathering and the like, especially habits of chasing carbon dioxide breath and seeking sex pheromones, to achieve environmentally friendly, pollution-free, and efficient killing of mosquitoes. Mosquito corpses are usually collected in a mosquito collection bin, which needs to be cleaned regularly, otherwise the mosquito corpses will emit an odor when they accumulate to a certain level, causing discomfort to users and affecting the user experience.

SUMMARY

A technical problem to be solved by the present application is how to provide an aromatherapy mosquito killer with an aromatherapy function, which can emit an aromatherapy smell during the mosquito killing process, eliminate the odor emitted by the mosquito corpses, and purify the air around the aromatherapy mosquito killer effectively, thereby improving the user experience.

A technical solution of the present application is to provide an aromatherapy mosquito killer, including:

a shell with a light chamber, a fan chamber and a mosquito killing chamber provided therein and arranged in sequence from top to bottom;

a light module arranged in the light chamber for emitting light outwardly;

a fan arranged in the fan chamber, a plurality of airflow holes being defined in top and bottom sides of a chamber wall of the fan chamber; and an aromatherapy box arranged in the mosquito killing chamber for collecting mosquitoes and storing aromatherapy, a plurality of ventilation holes being defined in a side wall and a top wall of the aromatherapy box;

wherein a plurality of air inlets and air outlets are defined in the shell, the air inlets, the airflow holes in the top side of the chamber wall of the fan chamber, the airflow holes in the bottom side of the chamber wall of the fan chamber, and the ventilation holes in the top wall of the aromatherapy box communicate with each other in sequence to form a mosquito-killing air duct for sucking in mosquitoes; and the ventilation holes in the side wall of the aromatherapy box communicate with the air outlets to form an exhaust air duct; and wherein an airflow generated by the fan flows through the mosquito-killing air duct and the exhaust air duct in sequence, and the ventilation holes in the side wall of the aromatherapy box are configured to prevent mosquitoes inside the aromatherapy box from passing through.

Compared with the prior art, the aromatherapy mosquito killer of the present application has the following advantages: the airflow generated by the fan can suck the mosquitoes into the aromatherapy box through the mosquito killing air duct, and at the same time the smell of the aromatherapy inside the aromatherapy box can dissipate outwardly through the exhaust air duct. On one hand, it can dry and kill the mosquitoes, and on the other hand, it also has the function of aromatherapy. That is, the present aromatherapy mosquito killer can emit the smell of aromatherapy during the mosquito killing process, eliminating the odor emitted by the mosquito corpses, and purifying the air around the aromatherapy mosquito killer effectively, thereby improving the user experience.

In some embodiments, the light module includes a lamp bead, a reflector, and a light circuit board, the lamp bead and the light circuit board are arranged inside the light chamber and connected to each other electrically; the reflector is arranged opposite to the lamp bead and extends out of the light chamber, and the reflector is configured for reflecting the light of the lamp bead outwardly. With such structure, the light of the lamp bead is reflected outwardly through the reflector, making the light emitted by the light module soft and easy to set into various lighting shapes.

In some embodiments, an inner space of the light chamber is configured to be cylindrical. With such structure, the light module emits light in the light chamber, so that the light chamber produces a visual effect of a burning candle, thereby improving the aesthetics of the aromatherapy mosquito killer.

In some embodiments, the chamber wall of the light chamber is translucent to the outside. With such structure, the brightness of the light module can be increased, so that the aromatherapy mosquito killer has the function of a night light.

In some embodiments, a plug-in shaft for hanging the reflector is provided in the light chamber, a magnetic block is provided at a bottom of the reflector, and an electromagnet corresponding to the magnetic block is provided on the light circuit board, and wherein the electromagnet is configured for generating a magnetic force on the magnetic block to drive the reflector to swing back and forth on the plug-in shaft. With such structure, by means of changing a current direction of a coil of the electromagnet coil, a direction of the magnetic force lines of the electromagnet can be changed continuously, so that the reflector can swing back and forth on the plug-in shaft. The light reflected by the swinging reflector 2-2 likes swaying candlelight of a burning candle, which is lifelike and improves the aesthetics of the aromatherapy mosquito killer.

In some embodiments, a bottom cover is provided at a bottom of the aromatherapy box and rotatably locked or unlocked with the shell at a bottom of the mosquito killing chamber, and the aromatherapy box is capable of being installed into the mosquito killing chamber or taken out from the bottom of the mosquito killing chamber together with the bottom cover. With such structure, it is convenient to assemble and/or disassemble the aromatherapy box, and it is also convenient to clean the aromatherapy box or place aromatherapy.

In some embodiments, an electric control chamber is provided in the shell and located out of the fan chamber and/or the mosquito killing chamber, and a power module, a switch and a charging port are provided in the electric control chamber, an electrical socket for installing the charging port and a touch portion for connecting the switch are provided on the shell, the power module is connected to the switch and the charging port electrically, and the switch is connected to the lighting assembly and the fan electrically. With such structure, the switch can be operated by the touching portion, which is convenient to use.

In some embodiments, a spring is provided in the electric control chamber with two ends thereof abutting the touch portion and the switch, respectively. With such structure, force can be transmitted to the switch through the spring, thereby operating the switch when the touch portion is pressed, so as to operate the switch, which is easy to use.

In some embodiments, the air inlets are arranged around the light chamber and above the fan chamber, and the air outlets are arranged around the mosquito killing chamber. With such structure, the mosquito-killing air duct and the exhaust air duct are smooth and unobstructed.

In some embodiments, the air outlets are arranged facing towards a bottom of the shell and higher than the bottom of the shell. With such structure, a position of the air outlets is higher than the bottom of the shell, so that the air outlets can be prevented from being blocked when the aromatherapy mosquito killer is placed on a table; the airflow enters the aromatherapy box, then flows downward out of the shell, and finally dissipates to the outside, avoiding physical discomfort caused by direct wind blowing to the outside, and enabling the smell of the aromatherapy to stay around the shell for a longer time, i.e., preventing the smell of the aromatherapy from dissipating too quickly.

AS SHOWN IN THE FIGURES

Figure 1:
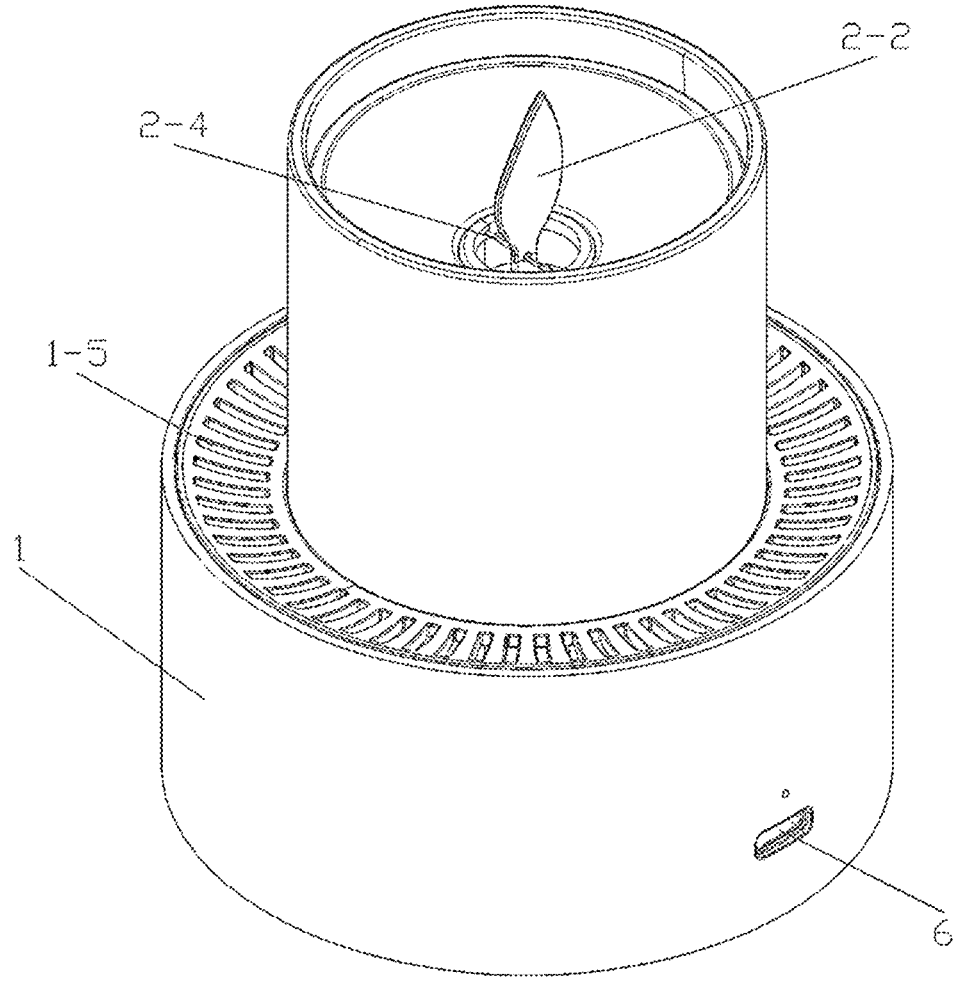
FIG. 1 is a schematic view of an aromatherapy mosquito killer according to an embodiment of the present application.

1, shell;
1-1, light chamber;
1-2, fan chamber;
1-21, airflow holes;
1-3, mosquito killing chamber;
1-4, electric control chamber;
1-41, electric socket;
1-42, touch portion;
1-5, air inlet;
1-6, air outlet;
2, light module;
2-1, lamp bead;
2-2, reflector;
2-3, magnetic block;
2-4, plug-in shaft;
2-5, electromagnet;
2-6, lighting circuit board;
3, fan;
4, aromatherapy box;

4-1, ventilation hole;
5, spring;
6, charging port; and
7, bottom cover.

DESCRIPTION OF THE EMBODIMENTS

For better understanding the present application, a more detailed description of the present application will be given below with reference to the append drawings. The append drawings exemplify one or more embodiments of the present application to make the understanding of the disclosed technical solutions more accurate and thorough. However, it should be understood that the present application can be implemented in various forms, not limited to the embodiments described below. In the specification, similar reference numerals refer to similar elements.

In the drawings, the thickness, size, and shape of objects have been slightly exaggerated for convenience of description. The drawings are illustrations only and are not drawn strictly to scale.

It should also be understood that the terms "comprise/comprises/comprising", "have/has/having", "include/includes/including" used in the specification, indicate the presence of the described features, integers, steps, operations, elements, and/or parts, but do not exclude the presence or addition of one or more other features, integers, steps, operations, elements, parts, and/or combinations thereof. Furthermore, expressions such as "at least one of" used after a list of features, refer the entire list of features rather than an individual element of the list of features.

Figure 3:
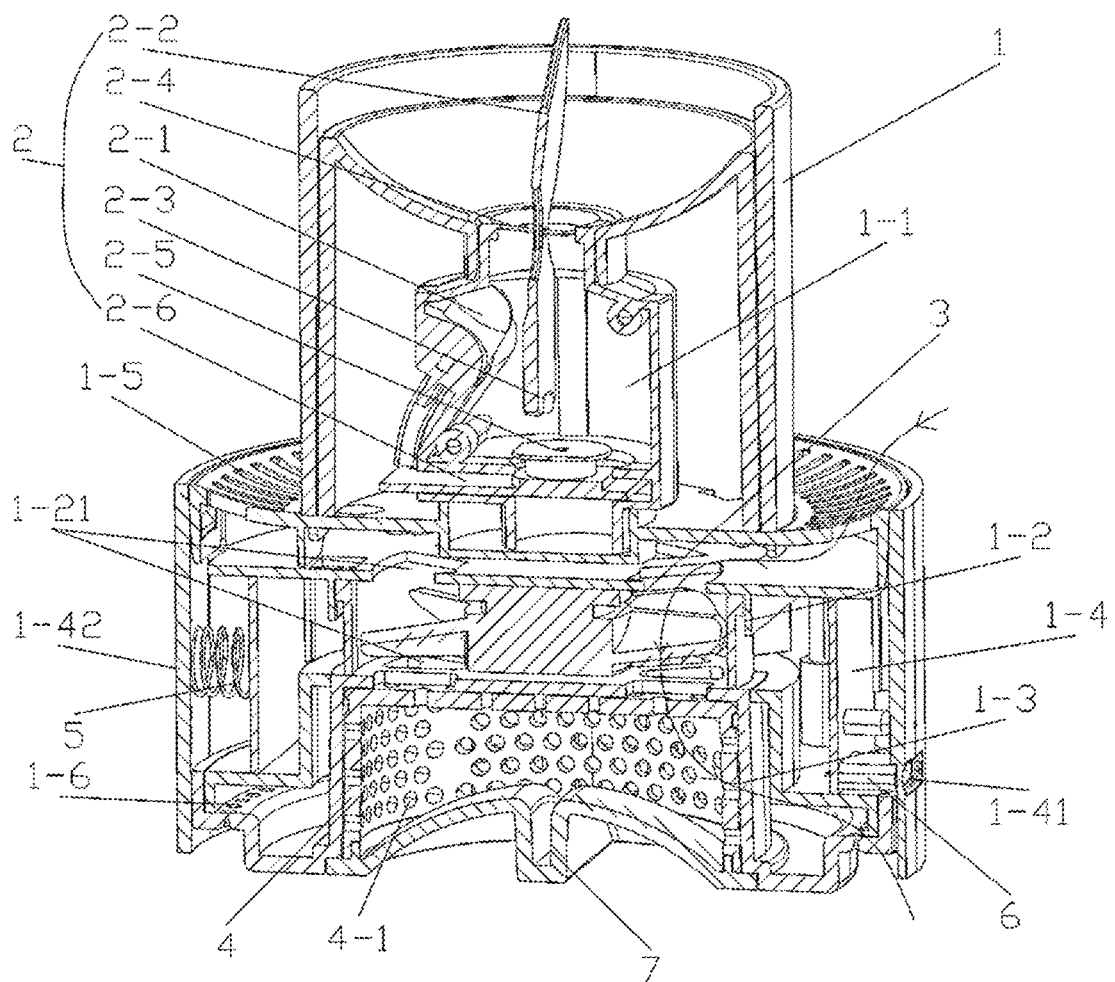
FIG. 3 is a schematic view of an internal structure of the aromatherapy mosquito killer.

As shown in FIG. 1 and FIG. 3, an aromatherapy mosquito killer according to an embodiment of the present application includes a shell 1 with a light chamber 1-1, a fan chamber 1-2 and a mosquito killing chamber 1-3 provided therein and arranged in sequence from top to bottom. An electric control chamber 1-4 is also provided in the shell 1, and located out of the fan chamber 1-2 and the mosquito killing chamber 1-3. A plurality of air inlets 1-5 and a plurality of air outlets 1-6 are defined in the shell 1, wherein the air inlets 1-5 are arranged around the light chamber 1-1 and above the fan chamber 1-2, and the air outlets 1-6 are arranged around the mosquito killing chamber 1-3 and face towards a bottom of the shell 1, wherein the air outlets 1-6 are higher than the bottom of the shell 1.

As shown in FIG. 1 and FIG. 3, an inner space of the light chamber 1-1 is configured to be cylindrical. A light module 2 is arranged in the light chamber 1-1, and includes a lamp bead 2-1, a reflector 2-2, and a light circuit board 2-6. The lamp bead 2-1 and the light circuit board 2-6 both are arranged inside the light chamber 1-1 and connected to each other electrically. The reflector 2-2 is arranged opposite to the lamp bead 2-1 and extends out of the light chamber 1-1, configured for reflecting the light of the lamp bead(s) 2-1 to the outside. A plug-in shaft 2-4 for hanging the reflector 2-2 is arranged in the light chamber 1-1, a magnetic block 2-3 is arranged at a bottom of the reflector 2-2, and an electromagnet 2-5 corresponding to the magnetic block 2-3 is arranged on the light circuit board 2-6. The electromagnet 2-5 may generate a magnetic force on the magnetic block 2-3 to drive the reflector 2-2 to swing back and forth on the plug-in shaft 2-4. A chamber wall of the light chamber 1-1 is translucent to the outside.

When the lamp bead 2-1 is powered, the light emitted by the lamp bead 2-1 passes through the entire light chamber 1-1 to the outside. The light circuit board 2-6 changes a current direction of a coil of the electromagnet continuously, causing a direction of the magnetic field lines of the coil of the electromagnetic to change continuously, accordingly the magnetic force that repels or attracts the magnetic blocks 2-3 also changes continuously, thereby driving the reflector 2-2 to swing back and forth on the plug-in shaft 2-4. The light reflected by the swinging reflector 2-2 likes swaying candle-light of a burning candle.

A fan 3 is arranged in the fan chamber 1-2, and a plurality of airflow holes 1-21 is defined in top and bottom sides of a chamber wall of the fan chamber 1-2.

Figure 2:
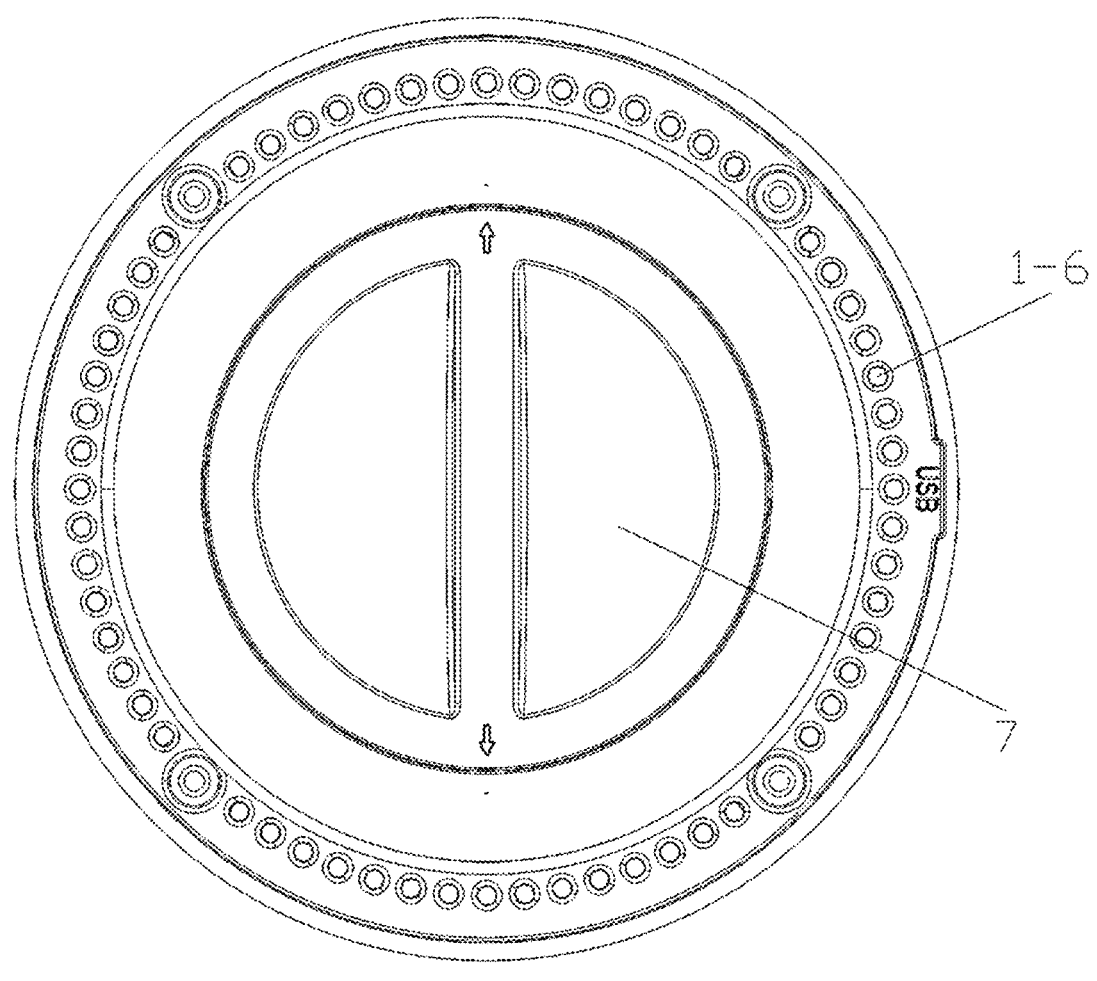
FIG. 2 is a schematic view of a bottom structure of the aromatherapy mosquito killer.

An aromatherapy box 4 is arranged in the mosquito killing chamber 1-3, configured for collecting mosquitoes and storing aromatherapy. A plurality of ventilation holes 4-1 is defined in a side wall and a top wall of the aroma-therapy box 4. As shown in FIG. 2 and FIG. 3, a bottom cover 7 is provided at a bottom of the aromatherapy box 4. The bottom cover 7 may be rotatably locked or unlocked with the shell 1 at a bottom of the mosquito killing chamber 1-3. The aromatherapy box 4 may be installed into the mosquito killing chamber 1-3 or taken out from the bottom of the mosquito killing chamber 1-3 together with the bottom cover 7.

The air inlets 1-5, the airflow holes 1-21 in an top side of the chamber wall of the fan chamber 1-2, the airflow holes 1-21 in the bottom side of the chamber wall of the fan chamber 1-2, and the ventilation holes 4-1 in the top wall of the aromatherapy box 4 communicate with each other in sequence and allow mosquitoes to pass through, coopera-tively forming a mosquito-killing air duct that can suck in mosquitoes. The ventilation holes 4-1 in the side wall of the aromatherapy box 4 communicate with the air outlets 1-6 to form an exhaust air duct, wherein the ventilation holes 4-1 are configured to prevent mosquitoes inside the aroma-therapy box from passing through.

As shown in FIG. 3, the airflow generated by the fan 3 may flow through the mosquito-killing air duct and the exhaust air duct in sequence, so that mosquitoes can be continuously sucked into the aromatherapy box 4 for drying, while the smell of the aromatherapy of the aromatherapy box 4 is dissipated to the outside, eliminating the odor emitted by the mosquito corpses, and purifying the air around the aromatherapy mosquito killer effectively.

The air inlets 1-5 are arranged around the light chamber 1-1, so that it is possible to utilize the phototactic behavior of the mosquitoes to induce the mosquitoes to fly closer, thereby improving the efficiency of mosquito killing. After the airflow enters the aromatherapy box 4, it flows down-ward through the air outlets 1-6 to the outside and then dissipates outwardly, avoiding physical discomfort caused by direct wind blowing outside, and enabling the smell of the aromatherapy to stay around the shell for a longer time, i.e., preventing the smell of the aromatherapy from dissi-pating too quickly.

As shown in FIG. 3, a power module, a switch and a charging port 6 are arranged in the electric control chamber 1-4, an electrical socket 1-41 for installing the charging port 6 and a touch portion 1-42 for connecting the switch are provided on the shell 1, a spring 5 is arranged in the electric control chamber 1-4 with two ends thereof in contact with the touch portion 1-42 and the switch, respectively, the power module is electrically connected to the switch and the charging port 6, and the switch is electrically connected to the lighting circuit board 2-6 of the light module 2 and the fan 3.

In this way, by simply pressing the touch portion 1-42, force can be transmitted to the switch through the spring, so that the switch is operated to make the light circuit board 2-6 and the fan 3 be powered on, thereby emitting "candlelight" to attract mosquitoes and starting the fan 3 to kill mosqui-toes. When the touch portion 1-42 is pressed again, the light circuit board 2-6 and the fan 3 are turned off, which is simple and convenient in operation.

The above are merely preferred embodiments of the present application, which are not intended to limit the present application. Any modifications, equivalent substitu-tions, and improvements made without departing from the spirit and principles of this application should fall within the scope of the present application.

The invention claimed is:

1. An aromatherapy mosquito killer, comprising:
   a shell with a light chamber, a fan chamber and a mosquito killing chamber provided therein and arranged in sequence from top to bottom;
   a light module arranged in the light chamber for emitting light outwardly;
   a fan arranged in the fan chamber, a plurality of airflow holes being defined in top and bottom chamber walls of the fan chamber; and
   an aromatherapy box arranged in the mosquito killing chamber for collecting mosquitoes and storing aroma-therapy, a plurality of ventilation holes being defined in a side wall and a top wall of the aromatherapy box;
   wherein a plurality of air inlets and air outlets are defined in the shell, the air inlets are located above the airflow holes of the top chamber wall in an axial direction of the shell and outside the airflow holes of the top chamber wall in a radial direction of the shell;
   the air inlets, the airflow holes in the top chamber wall of the fan chamber, the airflow holes in the bottom cham-ber wall of the fan chamber, and the ventilation holes in the top wall of the aromatherapy box communicate with each other in sequence to form a mosquito-killing air duct for sucking in mosquitoes; and the ventilation holes in the side wall of the aromatherapy box com-municate with the air outlets to form an exhaust air duct; and
   wherein an airflow generated by the fan flows through the mosquito-killing air duct and the exhaust air duct in sequence, and the ventilation holes in the side wall of the aromatherapy box are configured to prevent mos-quitoes inside the aromatherapy box from passing through.

2. The aromatherapy mosquito killer according to claim 1, wherein the light module comprises an LED, a reflector, and a light circuit board, the LED and the light circuit board are arranged inside the light chamber and connected to each other electrically; the reflector is arranged opposite to the LED and extends out of the light chamber, and the reflector is configured for reflecting the light of the LED outwardly.

3. The aromatherapy mosquito killer according to claim 2, wherein an inner space of the light chamber is cylindrical.

4. The aromatherapy mosquito killer according to claim 3, wherein the chamber wall of the light chamber is translucent to the outside.

5. The aromatherapy mosquito killer according to claim 3, wherein a plug-in shaft for hanging the reflector is provided in the light chamber, a magnetic block is provided at a bottom of the reflector, and an electromagnet corresponding to the magnetic block is provided on the light circuit board, and wherein the electromagnet is configured for generating a magnetic force on the magnetic block to drive the reflector to swing back and forth on the plug-in shaft.

6. The aromatherapy mosquito killer according to claim 2, wherein the light chamber comprises an annular side wall surrounding the LED and a curved top wall concaved inwardly from a top end of the annular side wall, and the reflector partly extends out of the light chamber through a central portion of the curved top wall.

7. The aromatherapy mosquito killer according to claim 1, wherein a bottom cover is provided at a bottom of the aromatherapy box and rotatably locked or unlocked with the shell at a bottom of the mosquito killing chamber, and the aromatherapy box is capable of being installed into the mosquito killing chamber or taken out from the bottom of the mosquito killing chamber together with the bottom cover.

8. The aromatherapy mosquito killer according to claim 1, wherein an electric control chamber is provided in the shell and located out of the fan chamber and/or the mosquito killing chamber, and a power module, a switch and a charging port are provided in the electric control chamber, an electrical socket for installing the charging port and a touch portion for connecting the switch are provided on the shell, the power module is connected to the switch and the charging port electrically, and the switch is connected to the light module and the fan electrically.

9. The aromatherapy mosquito killer according to claim 8, wherein a spring is provided in the electric control chamber with two ends thereof abutting the touch portion and the switch, respectively.

10. The aromatherapy mosquito killer according to claim 1, wherein the shell comprises a first wall on which the light chamber is arranged, the first wall comprises a first annular portion extending beyond the light chamber in the radial direction of the shell, and the air inlets are defined in the first annular portion, arranged around the light chamber and above the fan chamber.

11. The aromatherapy mosquito killer according to claim 10, wherein the shell further comprises a second wall being lockable with the mosquito killing chamber, the second wall comprises a second annular portion extending beyond the mosquito killing chamber in the radial direction of the shell, and the air outlets are defined in the second annular portion and higher than a bottom of the mosquito killing chamber.

12. The aromatherapy mosquito killer according to claim 11, wherein the shell further comprises a first cylindrical body, the first wall is coupled to a top end of the first cylindrical body, and the second wall is couple to a bottom end of the first cylindrical body, and the fan chamber and the mosquito killing chamber are received in the first cylindrical body.

13. The aromatherapy mosquito killer according to claim 12, wherein the shell further comprises a second cylindrical body arranged on the first wall and surrounding the light chamber, and the second cylindrical body has an outer diameter less than that of the first cylindrical body.

* * * * *